(12) United States Patent
Shibata et al.

(10) Patent No.: US 9,255,793 B2
(45) Date of Patent: Feb. 9, 2016

(54) DEFECT INSPECTION METHOD AND DEVICE THEREOF

(75) Inventors: Yukihiro Shibata, Fujisawa (JP); Toshifumi Honda, Yokohama (JP); Taketo Ueno, Kawasaki (JP); Atsushi Taniguchi, Fujisawa (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 714 days.

(21) Appl. No.: 13/521,086

(22) PCT Filed: Feb. 9, 2011

(86) PCT No.: PCT/JP2011/052787
§ 371 (c)(1),
(2), (4) Date: Jul. 30, 2012

(87) PCT Pub. No.: WO2011/099537
PCT Pub. Date: Aug. 18, 2011

(65) Prior Publication Data
US 2012/0296576 A1 Nov. 22, 2012

(30) Foreign Application Priority Data
Feb. 10, 2010 (JP) .................................. 2010-027702

(51) Int. Cl.
*G01N 21/55* (2014.01)
*G06F 19/00* (2011.01)
*G01B 11/30* (2006.01)
(Continued)

(52) U.S. Cl.
CPC ............ *G01B 11/303* (2013.01); *G01N 21/956* (2013.01); *H01L 21/67288* (2013.01)

(58) Field of Classification Search
CPC .................. H01L 2924/0002; H01L 21/67288; H01L 2924/00; H01L 22/12; H01L 22/26; G01N 21/956; G01N 21/9501; G01B 11/303
USPC ............. 702/35, 40; 356/237.1, 237.2, 237.3, 356/237.4
See application file for complete search history.

(56) References Cited

U.S. PATENT DOCUMENTS 6,501,545 B2 * 12/2002 Komuro et al. ............. 356/237.2
8,203,706 B2 * 6/2012 Shibata et al. ............. 356/237.2
(Continued)

FOREIGN PATENT DOCUMENTS

JP 2000-002664 1/2000
JP 2005-517906 6/2005
(Continued)

*Primary Examiner* — John H Le
(74) *Attorney, Agent, or Firm* — Baker Botts L.L.P.

(57) ABSTRACT

A defect inspection device includes an irradiation unit for simultaneously irradiating different regions on a sample with illumination light under different optical conditions, the sample being predesigned to include patterns repeatedly formed thereupon, wherein the patterns are to be formed in the same shape; a detection unit for detecting, for each of the different regions, a beam of light reflected from each region irradiated with the illumination light; a defect candidate extraction unit for extracting defect candidates under the different optical conditions for each of the different regions, by processing detection signals corresponding to the reflected light which is detected; a defect extraction unit for extracting defects by integrating the defect candidates extracted under the different optical conditions; and a defect classifying unit for calculating feature quantities of the extracted defects and classifies the defects according to the calculated feature quantities.

7 Claims, 10 Drawing Sheets

(51) Int. Cl.
*G01N 21/956* (2006.01)
*H01L 21/67* (2006.01)

(56) References Cited

U.S. PATENT DOCUMENTS 8,634,069 B2 * 1/2014 Nakano et al. ............ 356/237.1
2004/0156042 A1 8/2004 Vaez-Iravani et al.
2005/0185172 A1 8/2005 Ishimaru et al.
2009/0279079 A1 11/2009 Shibata et al.
2011/0149275 A1 6/2011 Nakano et al.

FOREIGN PATENT DOCUMENTS

| JP | 2009-192541 | 8/2009 |
| JP | 2009-257903 | 11/2009 |
| JP | 2009-276273 | 11/2009 |

* cited by examiner

DEFECT INSPECTION METHOD AND DEVICE THEREOF

TECHNICAL FIELD

The present invention relates to methods for inspecting defects, foreign matter, and other unwanted substances present on surfaces of microstructured patterns formed on samples through thin-film processes represented by semiconductor-manufacturing processes and flat-panel display manufacturing processes. The invention also relates to devices used in the above defect inspection methods.

BACKGROUND ART

Examples of prior-art semiconductor inspection device configurations include the configuration described in JP-T-2005-517906. This prior-art inspection device has a dark-field detection optical system that illuminates a wafer surface with laser light obliquely and detects the light scattered from the wafer surface. The optical system employs off-axis illumination in which the laser light is emitted from the outside of an objective lens. During off-axis illumination, if the optical system includes vertical detection optics having an optical axis parallel to a normal line relative to the surface of the wafer, the system needs to have a low elevation angle for illumination due to mechanical restrictions associated with disposition of the vertical detection optics.

On the other hand, JP-A-2000-2664 describes through-the-lens (TTL) illumination in which light is emitted through an objective lens having an optical axis vertical to a wafer. In the TTL illumination, the wafer can be illuminated substantially vertically.

PRIOR ART LITERATURES

Patent Document

Patent Document 1: JP-T-2005-517906
Patent Document 2: JP-A-2000-2664

SUMMARY OF THE INVENTION

Problem to be Solved by the invention

Various patterns are formed on semiconductor wafers. The kinds of defects also vary from cause to cause. Patterns represented by DRAMs (Dynamic Random Access Memories) and the like, are periodically wired patterns, and examples of serious defects influential upon a semiconductor device production yield include defects that can cause pattern short-circuiting, as well as scratches. In particular, short-circuiting defects at the groove bottom of an etched pattern prevent illumination light from reaching the groove bottom in such cases as too small an illumination elevation angle or too narrow an interconnecting pitch, and thereby reduce the amount of light scattered from the short-circuiting defects at the groove bottom. This is most likely to result in the defects being overlooked.

In addition, for a recessed defect such as a scratch, since increasing the illumination elevation angle provides a larger cross-sectional area for scattering, higher-elevation illumination enables a larger amount of light to be scattered from the scratch. For this reason, higher-elevation illumination is advantageous for detecting any groove bottom short-circuiting defects and scratches present on etched pattern surfaces.

The off-axis illumination described in prior-art Patent Document 1, however, has a problem in that the presence of the restrictions which make it absolutely necessary for the optical system to have a low elevation angle for illumination can become an obstruction to implementing high elevation angle illumination advantageous for detecting the above defects.

Additionally, although the TTL illumination described in prior-art Patent Document 2 enables high elevation angle illumination, the TTL illumination has a problem in that during dark-field detection that uses a spatial filter to block regularly reflected light, stray light such as lens-reflected light reaches an image surface and is thus likely to affect inspection sensitivity.

The present invention provides a dark-field defect detection method and related device based on high elevation angle illumination, the detection method and related device being adapted to resolve the above problems and thus during detection of any groove bottom short-circuiting defects and scratches present on etched pattern surfaces, prevent lens-reflected light and other stray light from reaching an image surface and affecting inspection sensitivity.

Means for Solving the Problems

In order to solve the above problems, a defect inspection method and related device according to a first aspect of the present invention is designed to: simultaneously irradiate different regions on a sample with illumination light under different optical conditions, on the surface of the sample patterns are repeatedly formed which are essentially having the same shape in design; detect, for each of the different regions, a beam of light reflected from each region simultaneously irradiated with the illumination light under the different optical conditions; extract defect candidates under the different optical conditions for each of the different regions, by processing detection signals corresponding to the beams of reflected light detected for each different region; extract defects by integrating the defect candidates extracted under the different optical conditions for each different region; and calculate feature quantities of the detected defects and classify the defects according to the calculated feature quantities.

Additionally, in order to solve the above problems, a defect inspection method and related device according to a second aspect of the present invention is designed to: irradiate, with first illumination light via an objective lens, a surface of a sample patterns are repeatedly formed which are essentially the same shape in design; obtain a first detection signal by detecting only reflected light which has passed through the objective lens and does not include regularly reflected light, of all reflected light from a region irradiated with the first illumination light; irradiate a surface of the sample with second illumination light from outside of the objective lens; obtain a second detection signal by detecting only reflected light which has passed through the objective lens and does not include regularly reflected light, of all reflected light from a region irradiated with the second illumination light; and detect defects on the sample by processing the first detection signal and the second detection signal.

Furthermore, in order to solve the above problems, a defect inspection method and related device according to a third aspect of the present invention is designed to: irradiate, with illumination light, a surface of a sample patterns are repeatedly formed which are essentially the same shape in design; simultaneously detect, under different detection conditions, a beam of light reflected from a region irradiated with the illumination light; extract defect candidates for each of the different detection conditions by processing detection signals for each of the different detection conditions, the detection signals being obtained during the simultaneous detection of the light reflections under the different detection conditions; extract defects on the sample by integrating the defect candidates extracted for each of the different optical conditions; and calculate feature quantities of the extracted defects and classify the defects according to the calculated feature quantities.

Effect of the Invention

In accordance with the present invention, images advantageous for more highly sensitive inspection of more easily identifiable defects can be obtained by efficiently detecting high elevation angle illumination light scattered from varieties of defects present on a wafer, such as groove bottom defects and scratches.

DESCRIPTION OF THE PREFERRED EMBODIMENTS

Hereunder, embodiments of the present invention will be described using the accompanying drawings.

First Embodiment

Figure 1:
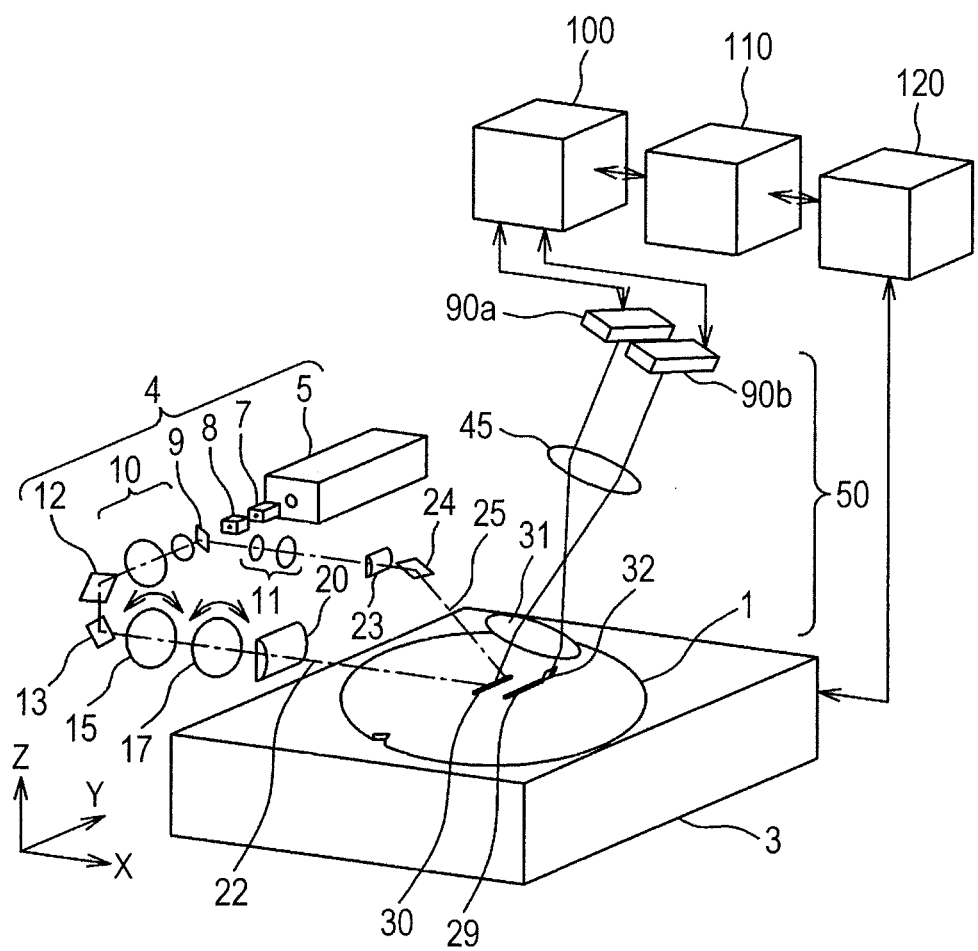
FIG. 1 is a block diagram showing a schematic configuration of optical systems based on off-axis illumination.

A configuration of a semiconductor wafer defect inspection device according to the present invention is shown in FIG. 1. A wafer 1 is mounted on a stage 3 and then a scanning direction of the stage and patterns formed on the wafer 1 are made parallel in a horizontal direction (this operation is referred to as O-alignment of the wafer 1), whereby coordinates are matched between a reference position of the wafer 1 and an X-Y coordinate system of the stage 3. The stage 3 can be moved independently in an X-Y plane and in a Z-direction perpendicular thereto, and is further constructed to be rotatable about an axis of a Z-direction. An illumination optical system 4, disposed obliquely to the wafer 1, linearly illuminates the surface of the wafer 1 with linear beams of illumination light, 29 and 30.

The illumination optical system 4 uses either a laser or a lamp, as its light source 5. In case a laser is used as the light source 5, the laser will be either a YAG second-harmonic 532-nm laser, third-harmonic 355-nm laser, fourth-harmonic 266-nm laser, 199-nm laser, or 193-nm laser, or some other laser that emits deep-ultraviolet (DW) light. A multispectral laser that oscillates at a plurality of wavelengths will be a further candidate. In case a lamp is used as the light source 5, candidates will be mercury lamps or mercury-xenon lamps that emit d-line (588 nm) light, e-line (546 nm) light, g-line (436 nm) light, h-line (405 nm) light, and/or i-line (365 nm) light. The embodiment shown in FIG. 1 uses a laser as the light source 5.

Laser light which is emitted from the laser light source 5 enters an electro-optic element 7 (such as LiNb03 or PLZT [short for (Pb, La)(Zr, Ti)03]) that can electrically control polarization in a predetermined direction. This electro-optic element may be replaced by a magneto-optic element formed from a garnet film, for example. Upon the polarizing direction being controlled, the amount of light passing through a polarizing beam splitter (PBS) 8 is reduced to a predetermined level and after the light has entered a beam splitter 9, part of the light reflects therefrom and the rest passes therethrough.

The light that has reflected from the beam splitter 9 is expanded in beam diameter by a beam expander 11, and then at a cylindrical lens 23, the expanded beam of light is converged in one direction and components at right angles to this converging direction are linearly shaped as parallel beams. This linearly shaped illumination light 25 reflects from a mirror 24 and enters a linear region 29 on the wafer 1 at incident angles of 45° to 90° to provide high elevation angle illumination, by utilizing a space created above the wafer 1 as a result of setting up an objective lens 31 slantwise with respect to a normal direction of the wafer 1.

On the other hand, the light that has passed through the beam splitter 9 enters a beam expander 10 and is expanded in beam diameter thereby. This expanded beam of light has its optical path oriented towards the wafer 1 by mirrors 12 and 13, and the beam is polarized to a predetermined state by a half wavelength plate 15 and a quarter wavelength plate 17, both rotatable. The polarization here is, for example, either S-polarization, P-polarization, linear polarization that generates oscillations at an angle somewhere in between S-polarization and P-polarization angles, or clockwise or counterclockwise elliptical polarization, with respect to the wafer 1. The illumination light 22, after passing through the half wavelength plate 15 and the quarter wavelength plate 17, is linearly shaped by a cylindrical lens 20 to conduct low elevation angle illumination of a linear region 30 (a thin line narrow in a direction of X and long in a direction of Y) on the wafer 1 at incident angles of 2° to 45°.

After the low-angle illumination (low elevation angle illumination) of the linear region 30 on the wafer 1 by the illumination light 22, of all components of the light scattered from the illuminated linear region 30, only those propagating within a numerical aperture (NA) of an objective lens 31, which is installed by inclining with respect to the normal line of the wafer 1, enter a detection optical system 50, thus forming an image on a detection surface (not shown) of an image sensor 90b via an image-forming lens 45.

Meanwhile, after the high elevation angle illumination of the linear region 29 on the wafer 1 by the illumination light 25, of all components of the light scattered from the linear region 29 to which the objective lens 31 is closer to the wafer 1 than the linear region 30 by the inclination of the objective lens 31, only components that are to have an elevation angle lower than the NA of the objective lens 31 are reflected within the NA of the objective lens 31 by a mirror 32. A distance from the linear region 29 via the mirror 32 to the objective lens 31 is made equal to a working distance (WD). Thus, of the light that has been scattered from the linear region 29 of the wafer 1, the components that have reflected from the mirror 32 and entered the objective lens 31 form an image on a detection surface (not shown) of an image sensor 90a via the image-forming lens 45.

This configuration of the wafer defect inspection device enables it to simultaneously detect the two kinds of dark-field images (formed by high elevation angle illumination and low elevation angle illumination) that differ in illumination elevation angle at spatially separate positions on the wafer 1. The spatially separate positions refer to the wafer linear region 29 irradiated with the illumination light 25, and the wafer linear region 30 irradiated with the illumination light 22. The image formed by the scattered light caused by the low elevation angle illumination light and detected by the image sensor 90a, and the image formed by the scattered light caused by the high elevation angle illumination light and detected by the image sensor 90b are input to an image-processing unit 100. Then, in the image-processing unit 100, input two images are compared with an image of the same pattern on design (e.g., an image of an adjacent die). Thus, defects are detected.

Defect determination and defect classification, both based on features and characteristics of images that differ in detection elevation angle, are also possible by position-matching the images of the same coordinates on the wafer 1 that have been detected by the image sensors 90a and 90b respectively. The image sensors 90a, 90b are, for example, charge-coupled device (CCD) or complementary metal-oxide semiconductor (CMOS) sensors, or a TDI (Time Delay Integration) operation type based on these sensors can be used as an alternative.

Figure 2:
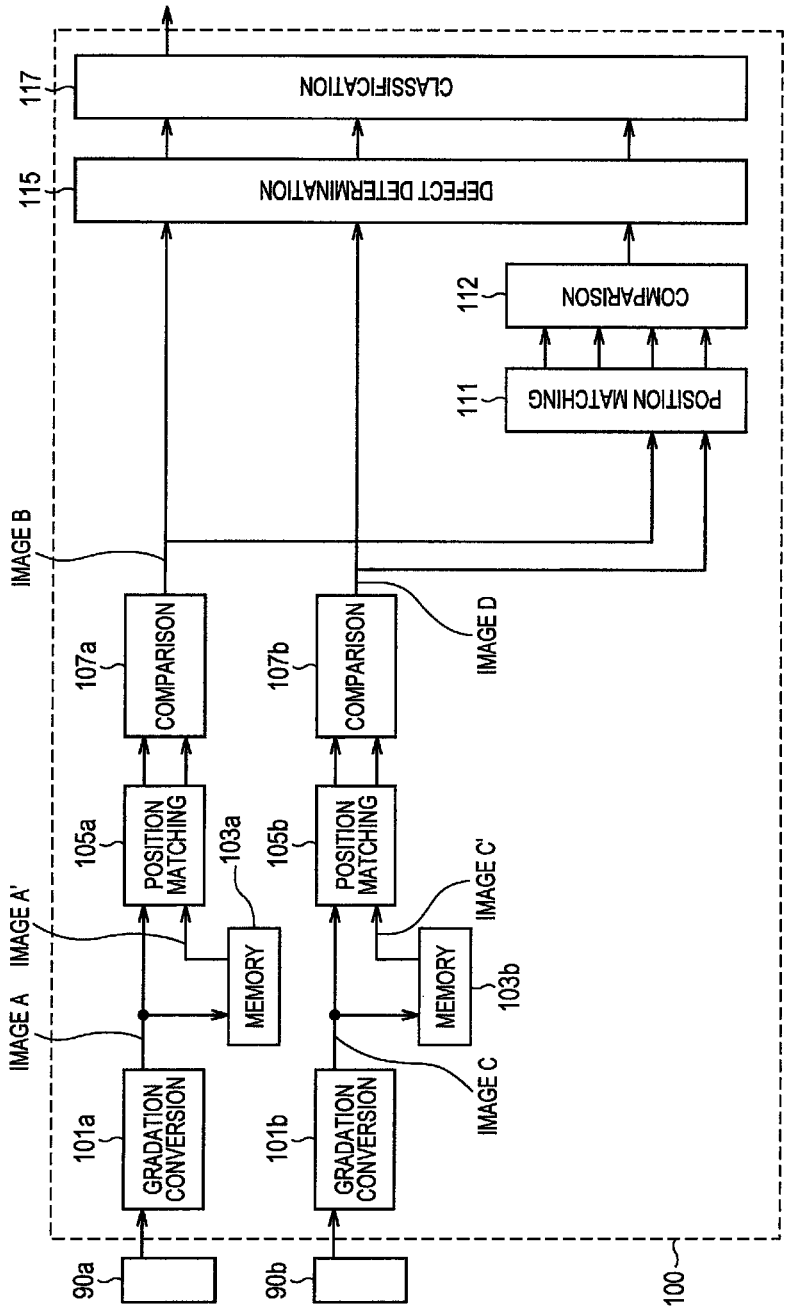
FIG. 2 is a block diagram showing a configuration of an image-processing unit in a first embodiment.

FIG. 2 shows a flow of processing by the image-processing unit 100 which conducts defect determination by processing the images detected by the image sensors 90a and 90b.

The image detected by the image sensor 90a is subjected to conversion of brightness, such as gamma(γ)-correction, in a gradation conversion unit 101a. The output image A from the gradation conversion unit 101a is divided in two and one of the two images A is sent to a position-matching unit 105a, and the other is sent to a memory 103a. The position-matching unit 105a receives, from the memory 103a, an image A' of a pattern which is essentially the same pattern in design (e.g., image of an adjacent die) that has already been detected by the image sensor 90a and stored into the memory 103a, and then matches positions of the images A and A'.

A comparator 107a creates a differential image B from the position-matched images A and A' by comparing the images A and A' with a threshold level that is either a previously set value or a value previously calculated from the detected images, and then calculates feature quantities of the differential image B as results of the comparisons. Next, a defect-determining unit 115 uses the feature quantities (such as a maximum contrast level and area) of the differential image B to determine whether the image contains defects.

Substantially the same processes as those described above are also conducted upon the image detected by the image sensor 90b. That is to say, the image detected by the image sensor 90b is subjected to the conversion of brightness, such as γ-correction, in a gradation conversion unit 101b. The output image C from the gradation conversion unit 101b is divided in two and one of the two images C is sent to a position-matching unit 105b, and the other is sent to a memory 103b. The position-matching unit 105b receives, from the memory 103b, an image C' of a pattern which is essentially the same pattern in design (e.g., image of an adjacent die) that has already been detected by the image sensor 90b and stored into the memory 103b, and then matches positions of the images C and C'.

A comparator 107b creates a differential image D from the position-matched images C and C' by comparing the images C and C' with a threshold level that is a previously set value or a value calculated from the detected images, and calculates feature quantities of the differential image D as results of the comparisons. Next, the defect-determining unit 115 uses the feature quantities (such as a maximum contrast level and area) of the differential image D to determine whether the image contains defects.

Additionally, the image comparison results by the comparators 107a, 107b are sent to a position-matching unit 111, in which the differential images B and D different in illumination elevation angle are then further matched in position. A differential image comparator 112 compares feature quantities of these differential images detected under the different optical conditions, and then the feature quantities are sent to the defect-determining unit 115 for defect determination. In this way, the defect-determining unit 115 uses the three kinds of feature quantities to conduct determinations. If any one of the three sets of determination results indicates that the corresponding image is defective, the feature quantities of the remaining two kinds of images are sent with the particular image to a classification unit 117 as information. The classification unit 117 classifies detected defects by kinds (e.g., foreign matter, etching residues, or scratches) or as dummy defects (such as non-uniformity in brightness of an oxide film, roughness of the pattern, grains, or other factors not critical or fatal to the semiconductor device). Coordinates, classification results, feature quantities, and others of the defects are sent to an operating unit 110, such that a user of the inspection device can display and output defect information data, a map of the defects on the wafer, and other defect information.

The coordinates, dimensions, and brightness of the detected defects, the features and characteristics of each defect that the differences in detection elevation angle will elucidate, and other defect information are sent to the operating unit 110, such that the user of the inspection device can check the display which outputs the defect information data, the on-wafer defect map, and other defect information.

The operating unit 110 also has a function for assigning operational instructions relating to the inspection device, and controls operation of a stage 3 and optical parts from a mechanism control unit 120 by giving operational instructions to the mechanism control unit 120. The detection optical system may have a spatial light modulator (not shown) on a Fourier transform plane of the wafer 1. The spatial light modulator displaced in that case may be a micro-shutter array that utilizes disposition of a metallic light-blocking rod or electro-optic effects of a birefringent element (such as LiNb03 or PLZT [short for (Pb, La)(Zr, Ti)03]). Alternatively, the spatial light modulator may be a liquid-crystal filter or a one-dimensional and two-dimensional array of filters that uses MEMS (Micro-Electro Mechanical Systems).

These devices can switch light transmitting/blocking rapidly by electrical control, and thus during inspection, enables changing to an appropriate filtering pattern according to a particular pitch and shape of a pattern 2 present on the wafer 1. In addition, to match height of a surface layer of the wafer 1 to a focal position of an objective lens 31, it is necessary to control wafer height by detecting the height of the wafer 1 and controlling a Z-axial position of the stage 3.

There is an optical lever method as an example of a method useable for wafer height detection. Although not shown, a height detection illumination system that obliquely illuminates a wafer 1 with slit light, and a height detection system that calculates wafer height by detecting the slit light reflected from the wafer 1 are arranged in the optical lever method. A difference between height of the wafer 1 and a focal position of an objective lens 31 is calculated and in case of a defocusing tolerance being overstepped, the mechanism control unit 120 instructs the stage 3 to adjust the height of the wafer 1 to the focal position. In the basic configuration described above, the inspection device continuously detects images while moving the stage 3 in one direction for constant speed scanning in the X-Y plane, and detects defects using the images.

Although the illumination regions 29 and 30 on the wafer 1 have been taken as an example of linear regions subjected to high elevation angle illumination and low elevation angle illumination, respectively, in the present embodiment, the high elevation angle illumination and low elevation angle illumination regions may be interchanged or both regions may be illuminated from the same elevation angle. Furthermore, polarization, illumination azimuths (directions of viewing angles relative to the X-axis when the wafer 1 is seen in plan view from above), illumination wavelengths, and other optical conditions may be changed for both of the illumination regions 29 and 30.

Still furthermore, there is a case having a characteristic in scattering directions, depending on defect sizes and kinds (short-circuiting defects, scratches, foreign substances, and so on). Simultaneously detecting low elevation angle illumination light and high elevation angle illumination light, therefore, enhances a possibility that the light scattered from various defects will be detected, and becomes advantageous for improving a capture ratio of defects.

Second Embodiment

Next, a second embodiment will be described. In the present embodiment, the detection optical system 50 in the configuration of FIG. 1 is disposed in a direction perpendicular to the wafer 1, high elevation angle illumination that uses illumination light 25 is made common in specifications to an optical axis of the detection optical system 50, and the same regions on the wafer are sequentially illuminated by changing optical paths.

Figure 3:
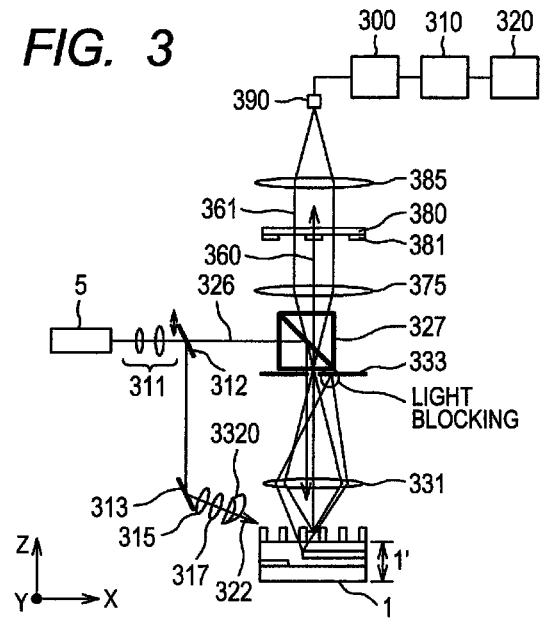
FIG. 3 is a block diagram showing a schematic configuration of TTL-illumination-based optical systems in a second embodiment.

FIG. 3 shows a configuration of a through-the-lens (TTL) type of optical system for conducting high elevation angle illumination via an objective lens 331. A laser light source is shown as 5, a beam expander as 311, an optical-path switching mirror as 312, a beam splitter as 327, a douser as 333, an objective lens 331, and a lens as 375. A spatial filter with a light-blocking element 381 is shown as 380, and an image-forming lens is shown as 385. Additionally, a mirror is shown as 313, a rotatable half wavelength plate as 315, a rotatable quarter wavelength plate as 317, and a cylindrical lens as 3320.

In this configuration, light which is emitted from the laser light source 5 enters the beam expander 311, then after being expanded in beam diameter thereby, travels straight forward without the optical path switching mirror 312 acting, and enters the beam splitter 327 disposed on the optical axis of the detection optical system. After being reflected by the beam splitter 327, the light further enters an opening device such as a linear opening for confocal detection or a pinhole array. The light that has passed through the opening device 333 provides the wafer 1 with high elevation angle illumination via the objective lens 331. Of the light scattered from the wafer 1, light that propagates into an NA of the objective lens 331 is captured by the objective lens 331 and once again passes through the opening device 333. The light, after further passing through the beam splitter 327 as well, reaches the lens 375 and forms a Fourier transform image of the wafer 1 on a surface having the spatial filter 380 disposed thereon. The spatial filter 380 includes the light-blocking element 381 that blocks regularly reflected light (0th-order light) and desired frequency components, and the light that has passed through regions other than the light-blocking element 381 forms the wafer image via the image-forming lens 385, on a surface having the image sensor 390 disposed thereon.

In this detection confocal optical system, since the opening device 333 blocks much of the stray light even if the illumination light reflects from the surface of the objective lens 331 and goes astray, a detection rate thereof by the image sensor 390 significantly decreases. This makes it possible to suppress stray light that has been a bottleneck in the blocking of regularly reflected light in the prior-art in combination of TTL illumination and spatial filters.

If the defects to be inspected are convexities such as foreign substances, using low elevation angle illumination, rather than increasing the NA of the objective lens 31 in combination with a high elevation angle illumination, may provide images advantageous for highly sensitive inspection. In such a case, laser light that has been emitted from the laser light source 5 is reflected downward, as shown in FIG. 3, by using the optical-path switching mirror 312. The thus-reflected light enters a mirror 322 and after passing through the half wavelength plate 315 and the quarter wavelength plate 317 as low elevation angle illumination light 322. After adjustment of this light in polarization state, the cylindrical lens 320 converges the light in one direction in a cross-sectional plane perpendicular to the optical axis of the laser. Components of the laser that are perpendicular to the converging direction are formed into parallel beams, thus providing the wafer 1 with off-axis illumination by obliquely illuminating the laser from the outside of the optical axis of the objective lens. Even with off-axis illumination, confocal detection is possible by matching the wafer region illuminated with the off-axis illumination light 22, nearly to an on-wafer projection image of the opening portion in the opening device 333. The light scattered from the wafer 1 illuminated by the off-axis illumination light 22 is captured by the objective lens 31 and then passes through the opening portion in the opening device 333. Light scattered from a lower-layer region of the wafer 1, on the other hand, becomes expanded light at the opened device 333, and much of the light is blocked by the opening device 333. The light scattered from the wafer surface-layer and passed through the opening device 333 passes through the beam splitter 327 and enters the lens 375. The light that has passed through the lens and the spatial filter 380 disposed on a Fourier transform plane forms a scatter image of the wafer 1 on the image sensor 390 via the lens 385.

Other beneficial effects of confocal detection are described below. The layer of the wafer 1 that is to be inspected is usually a top layer of the wafer surface, so defects present on lower layers having multilayer interconnects formed thereupon are generally excluded from detection. This is because, even if these lower-layer defects are to be detected, since the defects are not identifiable during reviewing with a scanning electron microscope (SEM), it cannot be confirmed whether they are defects. During confocal detection, if the objective lens 331 is properly focused on the surface layer of the wafer 1 that is to be subjected to defect detection, the light scattered from defects or the pattern present on the surface layer will pass through the opening portion in the opening device 333 and enter the beam splitter 327. Half of this incident light will pass through the beam splitter 327 first and then the lens 375, and the light, after further passing through the spatial filter 380, will enter the image-forming lens 385 and form each on-wafer defect image on a detection surface (not shown) of the image sensor 390. In contrast to this, the light scattered from the lower layers of the wafer 1 will be defocused and expanded at the opening device 333 and much of this light will be blocked by the opening device 333. The scattered light from the lower layers that become pseudo defects will therefore be nearly blocked, which will in turn be effective for suppressing the detection of the lower-layer defects.

Wafer structures and the kinds of defects are various, and optical conditions for obtaining images advantageous for highly sensitive inspection differ according to the particular subject of inspection. At many of semiconductor-manufacturing lines, optical conditions to be used for inspection are made appropriate for each manufacturing process. Accordingly, low elevation angle illumination, not high elevation angle illumination that includes vertical illumination, may be advantageous for highly sensitive inspection of some specific kinds of defects.

Figure 4:
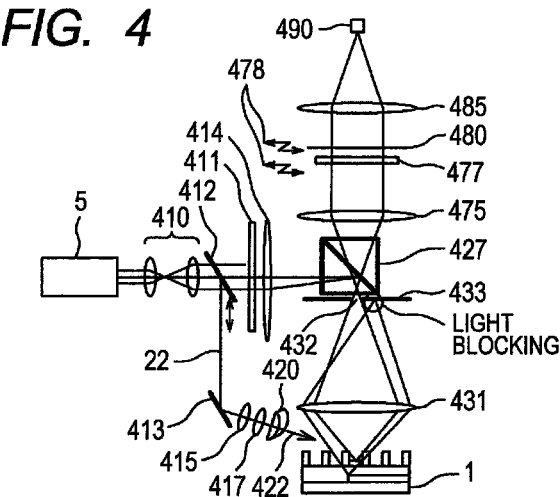
FIG. 4 is a block diagram showing a schematic configuration of a TTL-illumination-based vertical illumination optical system in the second embodiment.

For these reasons, a wide range of settable illumination conditions need to be provided beforehand to respond to such diversity of wafer structures and defect kinds. FIG. 4 shows an illumination optical system configuration controllable in illumination light elevation angle. The configuration shown in FIG. 4 is basically the same as the optical system configuration described in FIG. 3, but differs in that a beam expander 410, an opening device 411, and a lens 414 are included. Light which is emitted from a laser light source 5 is expanded in beam diameter by the beam expander 410, then after passing through an opening portion in the opening device 411, passes through the lens 414, and thus forms an image of the opening device 411 in a pupil position 432 of an objective lens 431. A section including a beam splitter 427 and an opening device 433 for confocal detection is of the same configuration and function as those described using FIG. 3.

An incident angle at which the wafer 1 is illuminated is determined according to the imaging position of an opening device 411 at the pupil of the objective lens 431. For example, if an image of the objective lens 431 is formed in a central position of the pupil, the illumination is vertical illumination relative to the wafer 1. On the other hand, if an image of the opening device 411 is offset with respect to an optical axis, the wafer 1 is obliquely illuminated within the range of the NA of the objective lens. For this reason, the opening portion in the opening device 411 is constructed to be changeable (controllable) in diameter, such that the incident angle at which the wafer 1 is illuminated can be controlled.

If the defects to be inspected are convexities such as foreign substances, using low elevation angle illumination, rather than increasing the NA of the objective lens 431 in combination with a high elevation angle illumination, may provide images advantageous for highly sensitive inspection. In such a case, laser light that has been emitted from a laser light source 5 is reflected downward, as shown in FIG. 4, by using an optical-path switching mirror 412. The thus-reflected light enters a mirror 413 and after passing through the half wavelength plate 415 and the quarter wavelength plate 417 as low elevation angle illumination light 422. After adjustment of this light in polarization state, a cylindrical lens 420 converges the light in one direction in a cross-sectional plane perpendicular to an optical axis of the laser. Components of the laser that are perpendicular to the converging direction are formed into parallel beams and this illumination light 422 provides the wafer 1 with off-axis illumination by obliquely illuminating the laser from the outside of the NA of the objective lens 431. Even with off-axis illumination, confocal detection is possible by matching the wafer region illuminated with the off-axis illumination light 422, nearly to an on-wafer projection image of the opening portion in the opening device 433.

The light scattered from the wafer 1 illuminated by the off-axis illumination light 422 is captured by the objective lens 431 and then passes through the opening portion in the opened device 433. Light scattered from a lower-layer region of the wafer 1, on the other hand, becomes expanded light at the opened device 433, and much of the light is blocked by the opening device 433. The light scattered from the wafer surface-layer and passed through the opening device 433 passes through the beam splitter 427 and enters the lens 475. The light that has passed through the analyzer 477 and the spatial filter 480 disposed on a Fourier transform plane forms a scatter image of the wafer 1 on the image sensor 490 via the lens 485.

Figure 5:
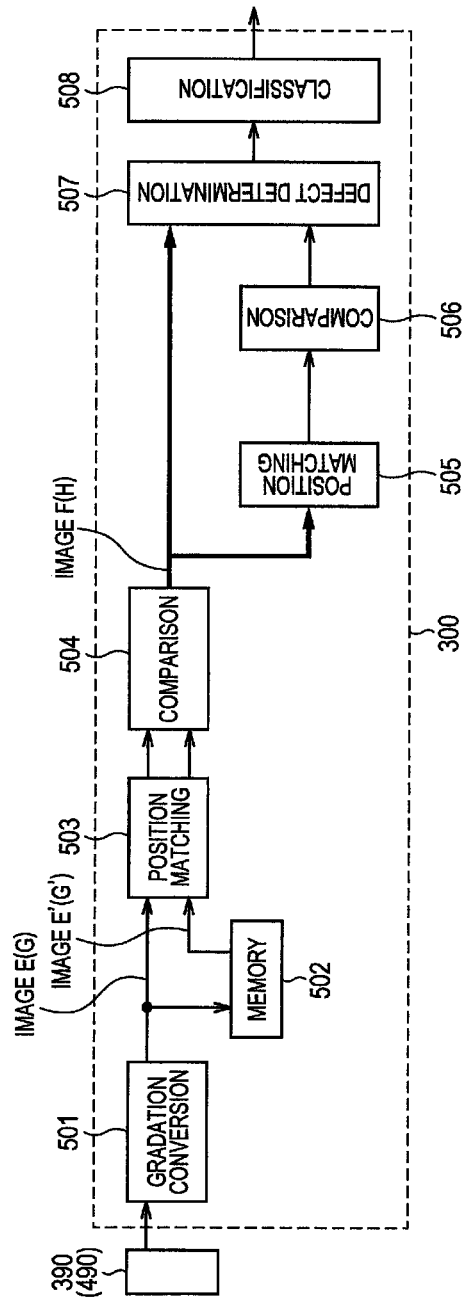
FIG. 5 is a block diagram showing a configuration of an image-processing unit in the second embodiment.

Next, a flow of processing conducted by an image-processing unit 300 which processes the image that has been detected by the image sensor 390 (490), and determines whether the image contains defects, is shown in FIG. 5.

The image $A_0$ detected during high elevation angle illumination by the image sensor 390 (490) is subjected to conversion of brightness, such as γ-correction, in a gradation conversion unit 501. The output image from the gradation conversion unit 501 is divided in two and one of two images E is sent to a position-matching unit 503, and the other (image E') is sent to a memory 502. The position-matching unit 503 receives, from the memory 502, an image E' of a pattern which is essentially the same pattern (e.g., image of an adjacent die) that has already been detected by the image sensor 390 (490) and stored into the memory 502, and then matches positions of the images E and E'.

A comparator 504 creates a differential image F from images E and E', the images of which are obtained from position-matching results, by comparing the images E and E' with a threshold level that is either a previously set value or a value previously calculated from the detected image, and then calculates feature quantities of the differential image F as results of the comparisons. Next, a defect-determining unit 507 uses the feature quantities (such as a maximum contrast level and area) of the differential image F to determine whether the image contains defects. The differential image F is also input to a position-matching unit 505.

Next, the image $G_0$ detected during low elevation angle illumination by the image sensor 390 (490) is subjected to the conversion of brightness, such as γ-correction, in the gradation conversion unit 501. The output image from the gradation conversion unit 501 is divided in two and one of two images G by the conversion is sent to the position-matching unit 503, and the other (image G') is sent to the memory 502. The position-matching unit 503 receives, from the memory 502, an image G' of a pattern which is essentially the same pattern in design (e.g., image of an adjacent die) that has already been detected by the image sensor 390 (490) and stored into the memory 502, and then matches positions of the image G and an image G'.

The comparator 504 compares the difference image H, the differential between the position-matched images G and G', with respect to a threshold level that is either a previously set value or a value previously calculated from the detected image, and then calculates feature quantities of the differential image H as results of the comparison. Next, the defect-determining unit 507 uses the feature quantities (such as a maximum contrast level and area) of the differential image D to determine whether the image contains defects. The differential image H itself is input to the position-matching unit 505.

The position-matching unit 505 matches positions of the differential images F and H that are images of the same place on the wafer 1, but different in illumination elevation angle. A differential image comparator 506 then compares feature quantities of these differential images F and H obtained using different conditions, and sends the feature quantities to the defect-determining unit 507 for defect determination. The defect-determining unit 507 conducts determinations using three kinds of feature quantities. If any one of the three sets of determination results indicates that the corresponding image is defective, the feature quantities including that of the remaining two kinds of images are sent to a classification unit 508. The classification unit 508 classifies detected defects by kinds (e.g., foreign matter, etching residues, or scratches) or as pseudo defects (such as non-uniformity in brightness of an oxide film, roughness of the pattern, grains, or other factors not critical or fatal to the semiconductor device). Coordinates, classification results, feature quantities, and others of the defects are sent to an operating unit 310, such that a user of the inspection device can check the display which outputs defect information data, a map of the defects on the wafer, and other defect information.

The coordinates, dimensions, and brightness of the detected defects, the features and characteristics of each defect that the differences in detection elevation angle will elucidate, and other defect information are sent to the operating unit 310, such that the user of the inspection device can check the display which outputs the defect information data, the on-wafer defect map, and other defect information.

Third Embodiment

Figure 6:
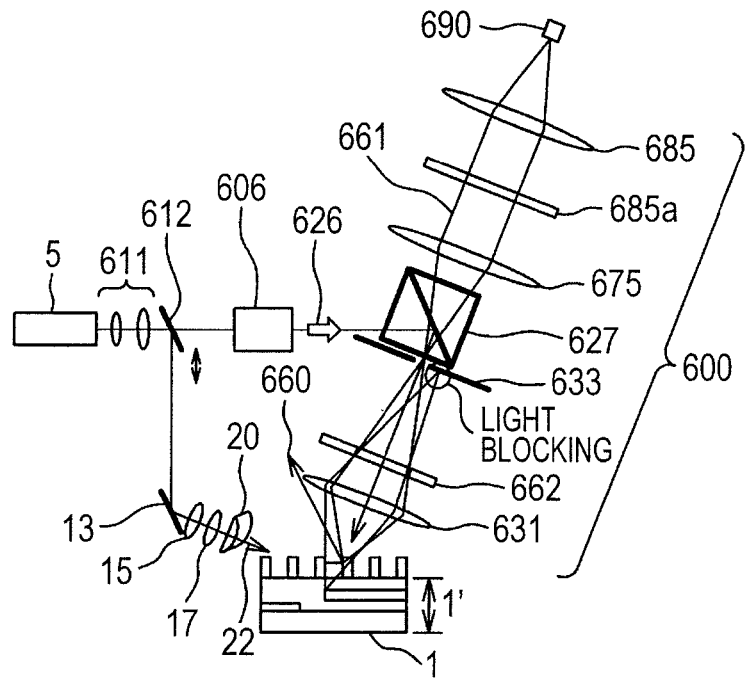
FIG. 6 is a block diagram showing a schematic configuration of a TTL-illumination-based oblique illumination optical system in a third embodiment, the optical system being constructed so as to prevent regularly reflected light from entering an objective lens.

The configuration in which the regularly reflected light from the wafer, by the TTL illumination, is blocked by a spatial filter, has been described and shown in the second embodiment. In the configuration of the second embodiment, forward-scattered light approximate to the regularly reflected light, that is, low-frequency components are detected. But some specific kinds of defects under inspection may strongly distribute back-scattered light (high-frequency components). The following describes a third embodiment relating to a scheme which uses TTL illumination to capture the light strongly distributed in back-scattered light. FIG. 6 shows an inspection device configuration that employs the scheme.

The present embodiment also employs high elevation angle illumination and low elevation angle illumination. low elevation angle illumination is of the same optical system configuration and light detection operation as those of the first and second embodiments, and description of the low elevation angle illumination optical system is therefore omitted. Referring to FIG. 6, in a high elevation angle illumination optical system that uses illumination light 626, when laser light is emitted from a laser light source 5, a laser beam axis control mechanism 606 controls a position of incidence, as well as an angle range, on a pupil 662 of an objective lens 631, and the light enters the objective lens 631 of an illumination and detection optical system 600 inclined relative to a normal line of a wafer 1. Admitting the laser light into a right side (see FIG. 6) of the inclined pupil 662 of the objective lens 631 correspondingly increases an incident angle relative to the wafer 1 and makes regularly reflected light 660 from a linearly illuminated region on the wafer 1 propagate through the outside of an NA of the objective lens 631 (the linear illumination uses the same method as that described in the second embodiment using FIG. 3). The light captured by the objective lens 631 is therefore backscattered light. A region in an optical path from a confocal detection opening device 633 to an image sensor 690 is substantially the same as that of FIG. 3 in terms of configuration.

Figure 7:
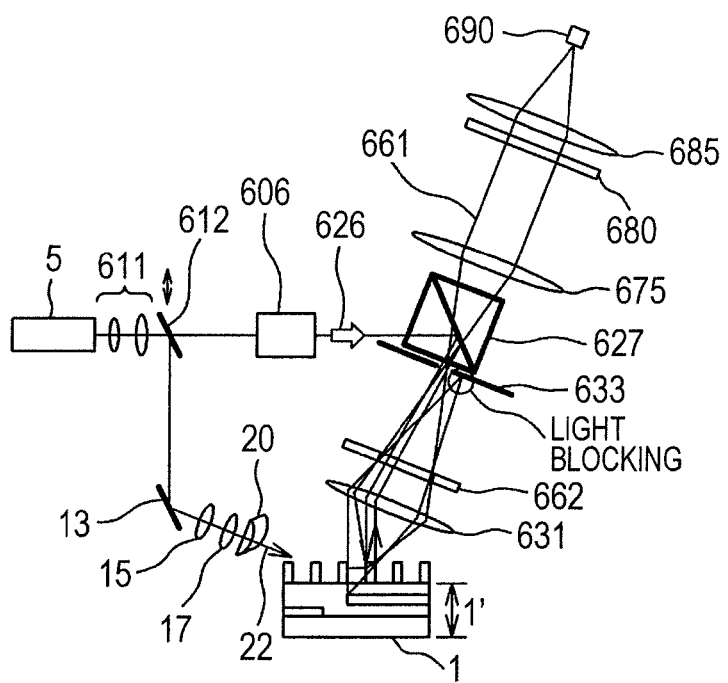
FIG. 7 is a block diagram showing a schematic configuration of a TTL-illumination-based oblique illumination optical system in a modification of the third embodiment, the optical system being constructed to cause regularly reflected light to enter an objective lens.

A technique for detecting forward-scattered light in this configuration is described below using FIG. 7. A basic configuration for the detection of forward-scattered light is the same as the configuration described in FIG. 6, and in the basic configuration, light that reaches the pupil 662 of the objective lens 631 is controlled by a laser beam axis control mechanism 606 to reach a portion close to the normal line of the wafer 1. Thus, the surface of the wafer 1 is illuminated with nearly vertical light at a higher angle of elevation than in the embodiment described in FIG. 6, and forward-scattered light that includes regularly reflected light is detected. The regularly reflected light is blocked by a spatial filter 680, and scattered light that has passed through the spatial filter 680 forms an image on the image sensor 690 via an image-forming lens 685.

Figure 8:
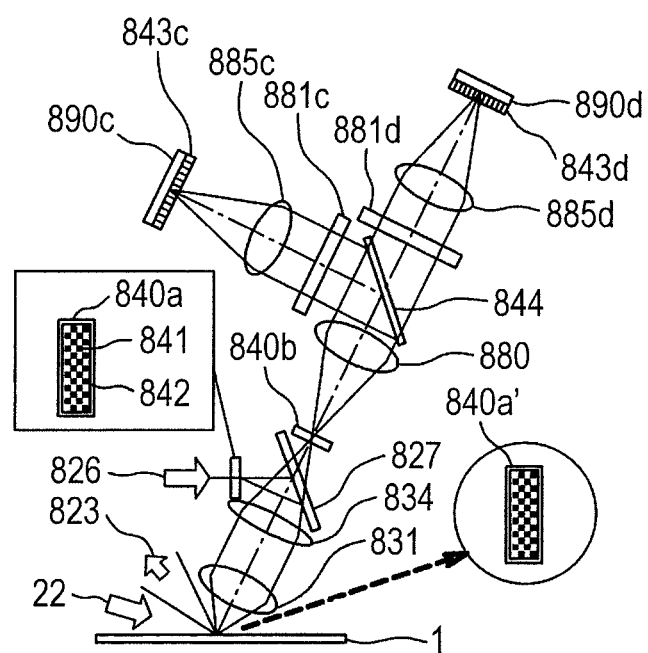
FIG. 8 is a block diagram showing a schematic configuration of a TTL-illumination-based oblique illumination optical system in another modification of the third embodiment, the optical system being constructed to irradiate a checkered pattern with illumination light and detect the light reflected from the pattern.

A modification of confocal detection optical system is shown in FIG. 8. In a basic configuration of the confocal detection optical system, its optical axis is inclined with respect to a normal-line direction of a wafer 1, as described in FIG. 6. Illumination light 826, which is emitted from a laser light source (not shown), enters an opening device 840*a* having a checker-patterned opening portion for confocal detection. The opening device 840*a* has a light-blocking element 842 in addition to the opening portion 841. An image of the opening device 840*a* is projected onto the wafer 1 via an image-forming lens 834 and an objective lens 831. Of the light that has been scattered from the wafer 1 illuminated with the illumination light 826, the light incident in the objective lens 831 passes through an illumination system/detection system branching mirror 827 via the image-forming lens 834 and forms an image on a detection surface.

An opening device 840*b* of a checkered pattern is placed on the image-forming plane. The opening portion 841 of the opening device 840*b* is disposed in conjugate relationship with respect to the image of the opening portion disposed in the illumination system. Light that has passed through the opening device 840*b* is branched by a polarized-beam splitter 844, and scattered light of specific frequencies is blocked by spatial filters 881*c*, 881*d* arranged in respective optical paths. Lights that have passed through the spatial filters either 881*c* or 881*d* enter opening devices 843*c*, 843*d* respectively for confocal detection, and only lights that have passed through openings in the opened devices either 843*c* or 843*d* enter image sensors either 890*c* or 890*d*.

An example of detecting images of the same space using two kinds of detection conditions (analyzing conditions and spatial filtering conditions) has been described and shown in the present embodiment. Thus, if a plurality of kinds of defects to be detected are present on the same wafer, detection conditions for exposing each defect can be assigned and detection sensitivity can be improved. While the example of using two systems to assign detection conditions in the present embodiment has been described, application to an example of using more detectors is also highly probable.

Fourth Embodiment

A fourth embodiment that relates to an optical system configuration consisting of a combination of the optical systems described in the first and third embodiments is described below using FIG. 9. The fourth embodiment employs two optical systems. One system uses high elevation angle TTL illumination light 926 with a laser light source 5, and the other system uses low elevation angle off-axis illumination light 22. The high elevation angle TTL illumination light linearly illuminates a region 930 on a wafer 1 (the illumination of the linear region 930 on the wafer 1 uses the same method as that described per FIG. 6). The off-axis illumination light 22 linearly illuminates a region 929 (the illumination of the linear region 29 on the wafer 1 uses the same method as those described in the first and second embodiments, so description of the off-axis illumination is omitted). A detection system has an axis inclined with respect to a normal line of the wafer 1, and of all light scattered from the regions 929 and 930, only the light scattered towards an objective lens 931 is captured by the objective lens 931.

Here, the light scattered at the region 929 present in the direction that the detection system is inclined with respect to the wafer 1 reaches a mirror 932 and works so that the light scattered at a lower-elevation side than an NA of the objective lens 931 will then propagate into the NA thereof. A distance from the illumination region 929 to the objective lens 931, and a distance from the illumination region 930 to the objective lens 931 are matched to a working distance (WD), whereby scatter images of the illumination regions can be formed in parallel on an image surface of the objective lens 931. An opening device 933 is disposed on the image surface, the opening device 933 having two confocal linear openings 9331 and 9332 that correspond to the scatter images. The image on the opening device 933 is enlarged and projected at lenses 980 and 985, with image sensors 991, 994 arranged at image positions corresponding to the linear openings 9331 and 9332.

While an example of subjecting the illumination region 930 to high elevation angle TTL illumination and the illumination region 929 to low elevation angle off-axis illumination has been taken in the description of the present embodiment, the subjects of the low elevation angle illumination and high elevation angle illumination may be interchanged. In addition, an embodiment in which polarizing and/or illuminating directions, illumination wavelengths, and other conditions differ at the illumination regions 929 and 930 would be probable.

Fifth Embodiment

Figure 9:
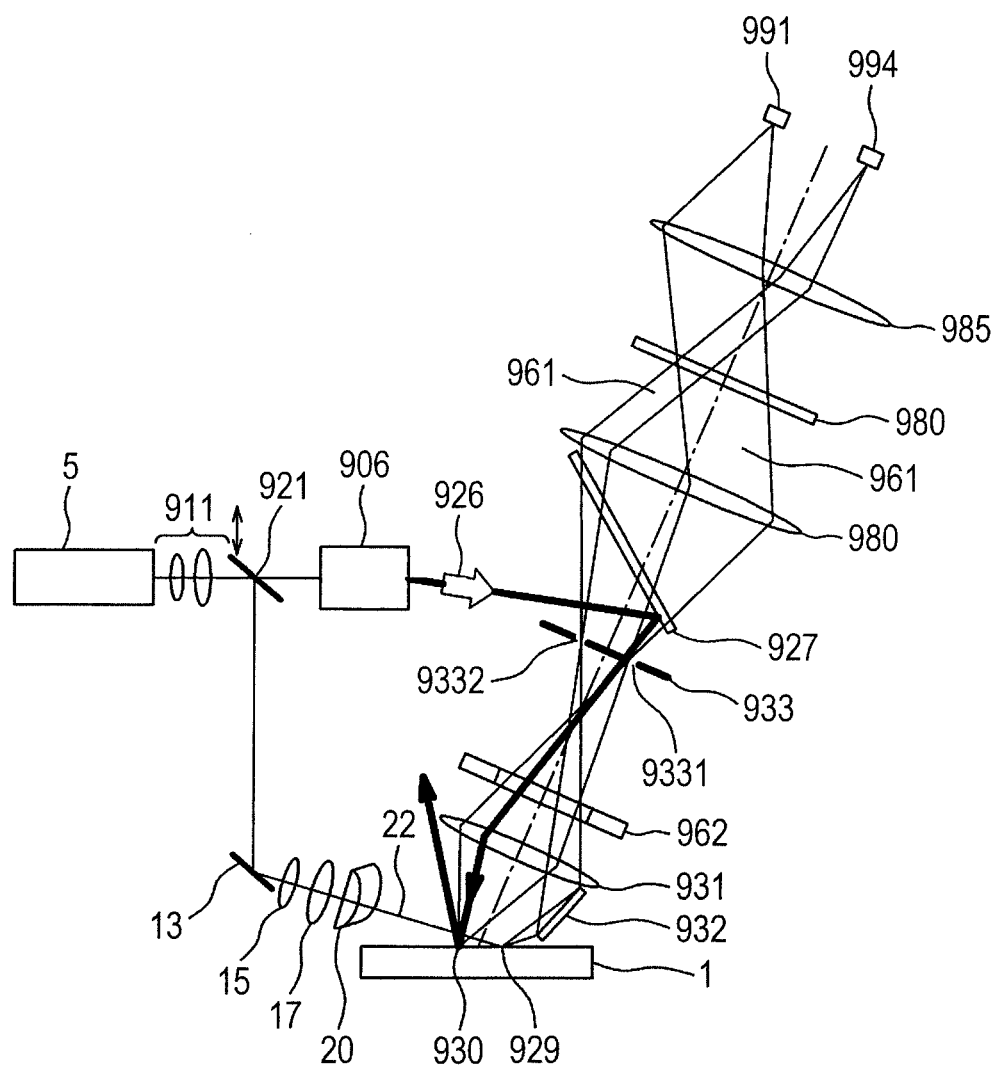
FIG. 9 is a block diagram showing a simultaneous illumination optical system configuration that uses off-axis illumination and TTL illumination in a fourth embodiment.
Figure 10:
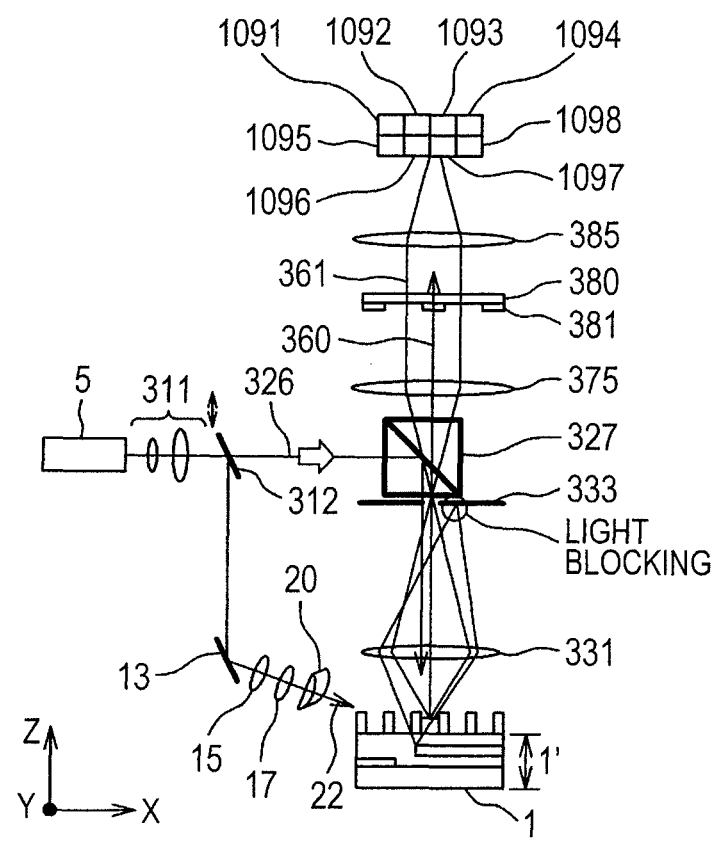
FIG. 10 is a block diagram showing a schematic configuration of a TTL-illumination-based vertical illumination optical system in a fifth embodiment, the optical system being constructed to detect a plurality of images different from one another in detection conditions.

The examples of detecting a plurality of images of different detection conditions by splitting one optical path into a plurality of paths have been shown in the detection systems described in FIG. 1 of the first embodiment, FIG. 8 of the third embodiment, and FIG. 9 of the fourth embodiment. The embodiment described below relates to detecting images of multiple sets of conditions without splitting an optical path of a detection system. FIG. 10 shows an optical system configuration that uses high elevation angle TTL illumination. Although layout of optical parts in this optical system is very similar to the configuration described in FIG. 3, the optical system differs in that it includes image sensors 1091 to 1094 and optical filtering devices 1095 to 1098 arranged in immediate front thereof (low elevation angle illumination of a wafer 1 uses the same method and same configuration as those described in the first and second embodiments, so description of the low elevation angle illumination is omitted). In immediate front of the image sensors 1091 to 1094, the optical filtering devices 1095 to 1098 each different in filtering characteristics are arranged for the image sensor 1091 to 1094 to detect four kinds of images that suit the filtering characteristics.

Figure 11:
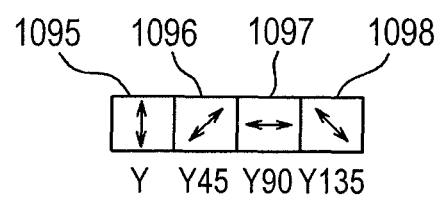
FIG. 11 is a plan view of a polarizing filter in the fifth embodiment.

FIG. 11 shows a polarizing-based filter array as an example of the optical filtering devices 1095 to 1098. The filter array is composed of an optical filtering device 1095, which uses a polarized-light transmitting axis parallel to a Y-direction, a device 1096, which forms an angle of 45° from the Y-direction, a device 1097, which forms an angle of 90° from the Y-direction, and a device 1098, which forms an angle of 135° from the Y-direction. This composition makes it possible to detect the four kinds of images different in analyzing conditions, in the same space on the wafer 1, and to perform comparative inspections with different polarization states of normal-pattern-scattered light and defect-scattered light as feature quantities.

A general image sensor is formed on a silicon substrate. However, a mode in which four sensors are arranged on one substrate and four images are output would be probable as a modification of the present invention. A photonic crystal with fine patterns laminated thereupon, a wire grid, a dielectric multilayer film structure, or the like are applicable as each optical filtering device.

Figure 12:
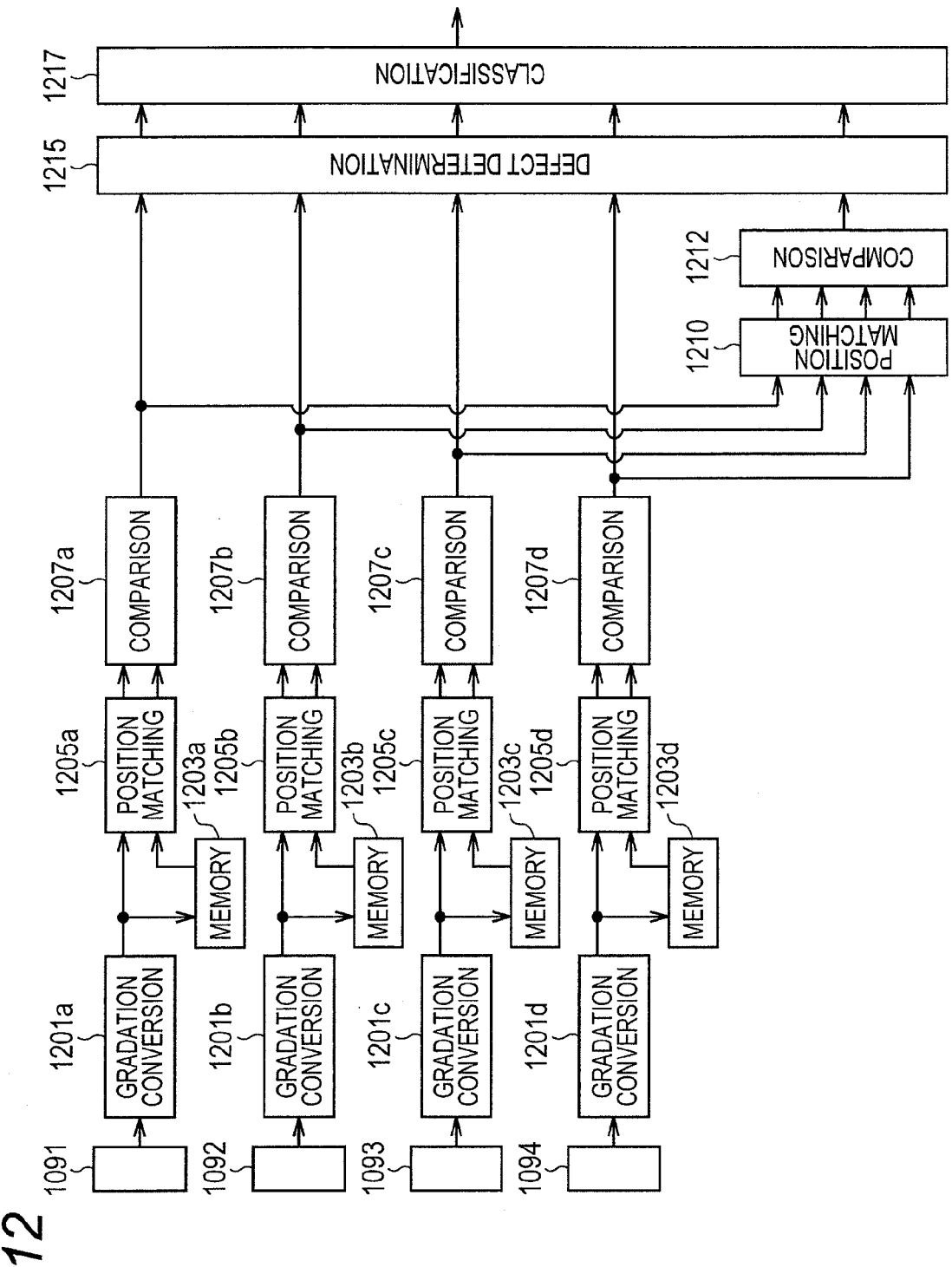
FIG. 12 is a block diagram showing a configuration of an image-processing unit in the fifth embodiment.

A flow of processing conducted by an image-processing unit 10100 is shown in FIG. 12. The image-processing unit 10100 processes the images that have been detected by the image sensors 1091-1094, and determines whether the images contain defects.

The image detected by the image sensor 1091 is subjected to conversion of brightness, such as γ-correction, in a gradation conversion unit 1201a. One of two images by the conversion is sent to a position-matching unit 1205a, and the other is sent to a memory 1203a. The position-matching unit 1205a matches a position of the image which has already been received directly from the conversion unit 1201a and a position of the image stored within the memory 1203a until does arrive the same predesigned pattern (e.g., image of an adjacent die) as that of the directly received image, and received from the memory 1203a. A comparator 1207a creates a differential image and the like from the two position-matched images by conducting comparisons, and then calculates feature quantities of the differential image as results of the comparisons. Next, a defect-determining unit 1215 uses the feature quantities (such as a maximum contrast level and area) of this differential image to determine whether the image contains defects.

Substantially the same processes as those described above are also conducted upon each of the images detected by the image sensors 1092, 1093, and 1094. Additionally, results of these image comparisons are sent to a position-matching unit 1210. Then, the position-matching unit matches the positions of the four images different in illumination elevation, detection elevation, and analyzing conditions. After comparison of feature quantities among the images of the different optical conditions, these feature quantities are sent to the defect-determining unit 1215, for defect determination. Therefore, the defect-determining unit 1215 conducts determinations using the five kinds of feature quantities in all. If any one of the five sets of determination results indicate that the corresponding image is defective, the feature quantities of the remaining four kinds are also sent to a classification unit 1217. The classification unit 1217 classifies detected defects by kinds (e.g., foreign matter, etching residues, or scratches) or as dummy defects (such as non-uniformity in brightness of an oxide film, roughness of the pattern, grains, or other factors not critical or fatal to the semiconductor device). After classifying, the classification unit 1217 outputs coordinates, classifying results, feature quantities, and others of the defects.

Figure 13:
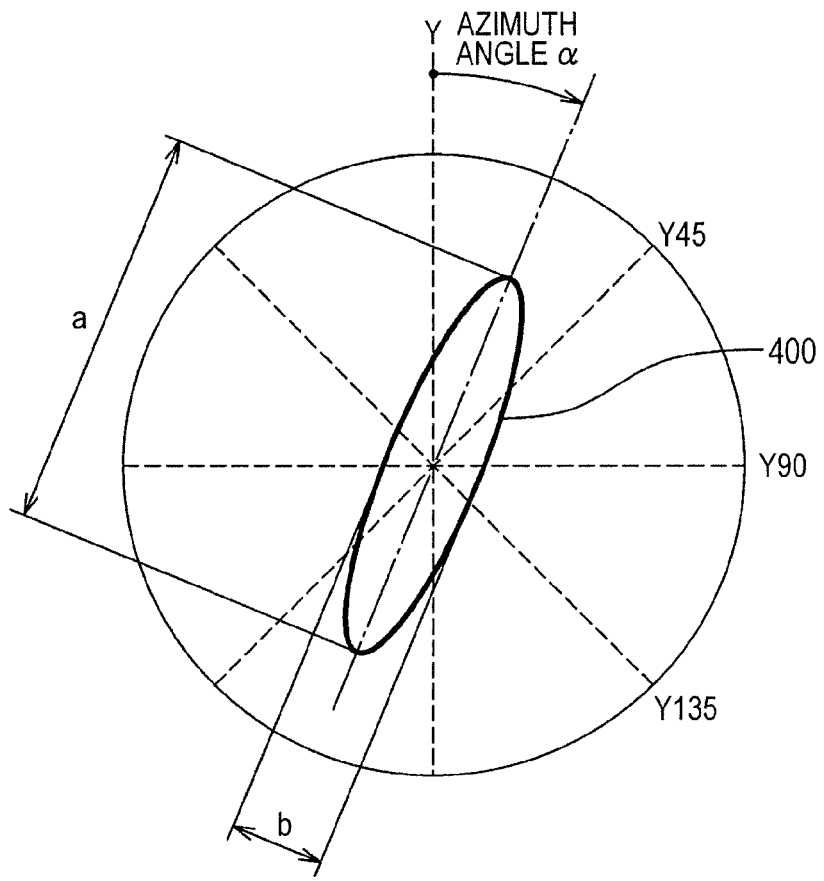
FIG. 13 is an azimuthal diagram of polarization that shows four kinds of polarized-light transmission axes in the fifth embodiment.
Figure 14:
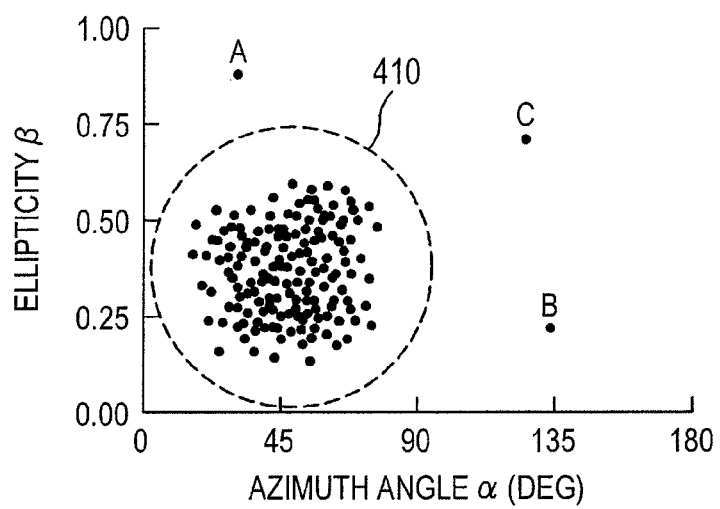
FIG. 14 is a scatter diagram of defects with an azimuth angle plotted on a vertical axis and ellipticity on a horizontal axis.

An example of feature quantities calculated from the four images which were detected using the different optical conditions is shown in FIG. 13. The optical system configuration that was adopted in this example is that shown in FIG. 10, and the four images in this example were detected using a polarized-light transmitting axis parallel to a Y-direction, and polarized-light transmitting axes angled at 45°, 90°, and 135° to the Y-direction. A polarization state 400 is calculated, pixel by pixel on the same space of the wafer, from each of the images. Indicators of the polarization state would be an azimuth a of elliptical polarization, and an ellipticity ("b/a") calculated in terms of a ratio between a major axis "a" and minor axis "b" of the ellipse. A defect-determining technique using these feature quantities is shown in FIG. 14. This figure shows a scatter diagram with the azimuth plotted as α on a horizontal axis and the ellipticity plotted as β on a vertical axis, the diagram being a schematic of data plots having the same coordinates in design pattern. Normal patterns are distributed in regions that resemble in both azimuth α and the ellipticity β. Points A, B, and C that overstep the distribution are determined as defect candidates.

While various combinations are possible for each of the configurations, functions, and image-processing details shown and described in the above embodiments, these combinations obviously fall under the scope of the present invention.

Industrial Applicability

The present invention can be applied to methods, and related devices, for inspecting defects, foreign matter, and other unwanted substances present on fine patterns formed on samples through a thin-film process in semiconductor-manufacturing processes and flat-panel display manufacturing processes.

DESCRIPTION OF REFERENCE NUMERALS

1 . . . Wafer, 3 . . . XYZθ stage, 4 . . . Illumination system, 5 . . . Laser, 6 . . . XYZθ stage, 7 . . . Electro-optic element, 10 . . . Beam expander, 15 . . . Rotatable half wavelength plate, 17 . . . Rotatable quarter wavelength plate, 22 . . . off-axis illumination light, 26 . . . TTL illumination light, 27 . . . Beam splitter, 29 . . . Illumination region, 30 . . . Illumination region, 31 . . . Objective lens, 32 . . . Mirror, 33 . . . Opened device for confocal detection, 40*a* . . . Opened device of checkered pattern, 62 . . . Pupil, 80 . . . Spatial modulator, 90 . . . Image sensor, 100 . . . Image-processing unit, 110 . . . Operating unit, 120 . . . Mechanism control unit, 130 . . . Height detection unit, 400 . . . Polarization state

The invention claimed is:

1. A defect inspection device comprising:
   irradiating unit which simultaneously irradiates different regions on a surface of a sample with illumination light under different optical conditions, on the surface of the sample patterns are repeatedly formed which are essentially having the same shape in design;
   detection unit which detects, for each of the different regions, light reflected from each region simultaneously irradiated with the illumination light under the different optical conditions by the irradiating unit;
   a first comparator which creates a first differential image from images of a first region under a first set of optical conditions;
   a second comparator which creates a second differential image from images of the first region under a second set of optical conditions;
   a differential image comparator which creates a third differential image based at least on the first differential image and the second differential image;
   a defect determination unit which determines defects based at least on feature quantities of the first differential image, feature quantities of the second differential image, and feature quantities of the third differential image; and
   defect classifying unit which classifies the defects.

2. The defect inspection device according to claim 1, wherein:
   the irradiating unit irradiates different linear regions on the sample, with beams of illumination light simultaneously and linearly formed under different optical conditions.

3. The defect inspection device according to claim 1, wherein:
   the irradiating unit simultaneously irradiates the sample under optical conditions of different incident angles of the illumination light upon the sample.

4. A defect inspection device comprising:
   a first irradiating unit which irradiates, with first illumination light via an objective lens, a surface of a sample patterns are repeatedly formed which are essentially the same shape in design;
   a second irradiating unit which irradiates the sample with second illumination light from an exterior of the objective lens;
   reflected-light detection unit which obtains a first detection signal by detecting only reflected light which has passed through the objective lens and does not include regularly reflected light, of all reflected light from a region irradiated with the illumination light by the first irradiating means, the reflected-light detection unit further obtains a second detection signal by detecting only reflected light which has passed through the objective lens and does not include regularly reflected light, of all reflected light from a region irradiated with the illumination light by the second irradiating unit;
   a comparator which creates a first differential image from images of a first region under illumination of the first irradiating unit and creates a second differential image from images of the first region under illumination of the second irradiating unit;
   a differential image comparator which creates a third differential image based at least on the first differential image and the second differential image; and
   a defect determination unit which detects defects based at least on feature quantities of the first differential image, feature quantities of the second differential image, and feature quantities of the third differential image.

5. The defect inspection device according to claim 4, wherein:
   the first irradiating unit emits the first illumination light via the objective lens from a direction inclined with respect to a normal-line direction of the surface of the sample.

6. A defect inspection device comprising:
   illumination light irradiator which irradiates a surface of a sample with illumination light, on the surface of the sample patterns are repeatedly formed which are essentially having the same shape in design;

reflected-light detector which simultaneously detects, under different detection conditions, a beam of light reflected from a region illuminated with the illumination light by the illumination light irradiator;

a first comparator which creates a first differential image from images of the region under a first set of detection conditions;

a second comparator which creates a second differential image from images of the region under a second set of detection conditions;

a differential image comparator which creates a third differential image based at least on the first differential image and the second differential image;

a defect determination unit which determines defects based at least on feature quantities of the first differential image, feature quantities of the second differential image, and feature quantities of the third differential image; and defect classifier which classifies the defects.

7. The defect inspection device according to claim 6, wherein:

the detection conditions under which the reflected-light detector detects reflected light are polarizing conditions of the reflected light.

* * * * *